United States Patent
Forssmann

(10) Patent No.: US 11,124,540 B2
(45) Date of Patent: Sep. 21, 2021

(54) POLYPEPTIDES FOR THE TREATMENT OF DISEASES

(71) Applicant: Neopep Pharma GmbH & Co., KG, Hanover (DE)

(72) Inventor: Wolf-Georg Forssmann, Hanover (DE)

(73) Assignee: Neopep Pharma Gmbh. & Co., Hanover (DE)

( * ) Notice: Subject to any disclaimer, the term of this patent is extended or adjusted under 35 U.S.C. 154(b) by 0 days.

(21) Appl. No.: 16/637,851

(22) PCT Filed: Sep. 10, 2018

(86) PCT No.: PCT/EP2018/074272
§ 371 (c)(1),
(2) Date: Feb. 10, 2020

(87) PCT Pub. No.: WO2019/048666
PCT Pub. Date: Mar. 14, 2019

(65) Prior Publication Data
US 2020/0247850 A1    Aug. 6, 2020

(30) Foreign Application Priority Data

Sep. 8, 2017 (EP) ..................... 17190152
Dec. 4, 2017 (EP) ..................... 17205238

(51) Int. Cl.
| | | |
|---|---|---|
| *A61K 38/00* | (2006.01) | |
| *A61K 38/08* | (2019.01) | |
| *A61K 38/10* | (2006.01) | |
| *A61P 35/00* | (2006.01) | |
| *C07K 7/08* | (2006.01) | |
| *C07K 1/18* | (2006.01) | |
| *C12N 15/63* | (2006.01) | |
| *G01N 33/68* | (2006.01) | |

(52) U.S. Cl.
CPC ............ *C07K 7/08* (2013.01); *A61P 35/00* (2018.01); *C07K 1/18* (2013.01); *C12N 15/63* (2013.01); *A61K 38/00* (2013.01); *G01N 33/6812* (2013.01)

(58) Field of Classification Search
CPC ........ A61K 38/00; A61K 38/08; A61K 38/10; A61P 35/00; C07K 7/08; C07K 1/18
See application file for complete search history.

(56) References Cited

U.S. PATENT DOCUMENTS 9,045,563 B2 * 6/2015 Forssmann ............. A61P 37/00

FOREIGN PATENT DOCUMENTS

| WO | 2009-004054 A2 | 1/2009 |
| WO | 2014-198834 A1 | 12/2014 |

OTHER PUBLICATIONS

Kuil et al., "Hybrid Peptide Dendrimers for Imaging of Chemokine Receptor 4 (CXCR4) Expression", Molecular Pharmaceutics, vol. 8, No. 6, pp. 2444-2453, (Dec. 5, 2011).
MacDonald et al., "Solid-Phase Synthesis of Phosphonylated Peptides", SYNLETT, vol. 2010, No. 13, pp. 1951-1954, (Aug. 1, 2010).
Search Report for copending European Patent Application No. PCT/EP2018/074272 dated Nov. 14, 2018.

* cited by examiner

*Primary Examiner* — Julie Ha
(74) *Attorney, Agent, or Firm* — Christensen Fonder Dardi; Elizabeth Gallo; Peter Dardi

(57) ABSTRACT

A polypeptide having the general amino acid sequence $Z^1IX^2RWX^5X^6KX^8PX^{10}X^{11}SZ^3$, wherein
$X^2$=V, M or L,
$X^5$=S or T,
$X^6$=K or R,
$X^8$=V, M, L or F,
$X^{10}$=Q or C,
$X^{11}$=V, M or F;
$Z^1$=0, $Z^2$, or pyro glutamate, wherein $Z^2$ is a modification of the amino group of the N-terminal amino acid having the structure —NR$^2$R$^3$ wherein R$^2$ and/or R$^3$ are independently from each other H or an acyl, alkyl, aryl, aralkyl, cyclo alkyl and heterocyclo alkyl group;
$Z^3$=0, or $Z^4$, wherein $Z^4$ is a modification of the carboxyl group of the C-terminal amino acid having the structure —C(O)—O—R$^1$ or —C(O)—NR$^2$R$^3$, wherein R$^1$ is an alkyl, aryl, aralkyl, cyclo alkyl and heterocyclo alkyl group; and R$^2$ and R$^3$ are defined as above.

6 Claims, No Drawings

Specification includes a Sequence Listing.

POLYPEPTIDES FOR THE TREATMENT OF DISEASES

This application is a National Stage filing of PCT Application No. PCT/EP2018/074,272 filed Sep. 10, 2018, entitled "POLYPEPTIDES FOR THE TREATMENT OF DISEASES", which claims priority to European Patent Application Nos. 17190152.3 filed Sep. 8, 2017, and 17205238.3 filed Dec. 4, 2017, all of which are incorporated herein by reference.

The present invention concerns polypeptides in particular their therapeutic uses as well as a method for manufacturing the peptides of the invention.

BACKGROUND OF THE INVENTION

When cells move, grow and differentiate in the body, so-called chemokines (attractants) are involved. These influence the cells via chemokine receptors on their surface. One of these receptors, CXC chemokine receptor 4 (CXCR4), activates rapid growth in cancer cells and migration, forming metastases throughout the body, preferentially in the lung, bone and liver. Most types of cancer become more aggressive through a chemokine receptor, if the receptor is up-regulated.

The CXCR4 is a G protein-coupled receptor (GPCR) with stromal cell-derived factor-1 (SDF-1 or CXCL12) as sole published ligand. CXCR4 is involved in multiple developmental and physiological processes including stem cell homing (Mohle and Drost, 2012) and migration of immune cells (Campbell et al., 2003). The CXCR4-CXCL12 axis also plays a role in innate and adaptive immunity, as well as in various disease processes, such as cancer cell metastasis, leukemia cell migration, rheumatoid arthritis and pulmonary fibrosis (Nagasawa et al., 1996; Zou et al., 1998; Tachibana et al. 1998; Furze et al., 2008). Man-made CXCR4 antagonists are capable of mobilizing hematopoietic stems cells (HSCs), which are utilized for immune reconstitution after organ transplantation or chemotherapy (Ratajczak and Kim, 2012; Schroeder and DiPersio, 2012). In addition, CXCR4 is also a major co-receptor for HIV-1 entry into target cells (Feng et al., 1996; Bleul et al., 1996). Co-receptor utilization of CXCR4 is highly effective and a high proportion of CD4+ T cells express this GPCR in lymphatic tissues in vivo. Nonetheless, almost exclusively HIV-1 variants utilizing the C-C chemokine receptor type 5 (CCR5) are transmitted and found during chronic HIV-1 infection (Alkhatib et al., 1996; Deng et al., 1996; Dragic et al., 1996). It has been proposed that multiple factors contribute to the inefficient transmission of CXCR4-tropic (X4) HIV-1 strains (Margolis and Shattock, 2006). However, the mechanism(s) underlying the effective control of X4 HIV-1 in immunocompetent individuals remain poorly understood.

Research on CXCR4-antagonists has recently become an immense field of projects due to the manifold indications In particular the efforts to find a strategy to intervene with cancer cell proliferation, differentiation, and metastasis was not so successful in clinical studies yet as expected. The development of one of the compound groups, namely AMD3100 a CXCR4-antagonists (a bicyclame compound: Hendrix and Flexner 2000), had to be stopped for long term treatments due to toxic side effects. Although AMD3100 is registered for single short applications in stem cell mobilisation, it is nevertheless a challenge to find adequate antagonists to the target CXCR4.

Terjee, S. et al. reviewed recently in Adv Cancer Res.2014; 124: 31-82 about the role of CXCR4 in cancer.

WO 2009/004054 A2 discloses a peptide having the amino acid sequence Z1-LVRYTKKVPQVSTPTL-Z2 (ALB-408) and its biologically active fragments and/or variants and/or derivatives, especially amidated, acetylated, sulfated, phosphorylated and/or glycosylated derivatives, and peptides obtainable by multiple synthesis which have the biological activity of ALB408-423; wherein Z represents number of from 0 to 10 amino acid residues.

WO 2014/198834 A1 discloses peptides, in particular dimers, effective in blocking the CXC-chemokine receptor 4 (CXCR4) mediated HIV-1 NL4-3 (X4-tropic) infection with an IC50 value of less than 50 μM.

An object of the invention is to provide peptides which inhibit proliferation of cancer cells, metastasis and show the types of cancers which are addressed by the different analogs and also reaction of antiinflammatory allergic reactions.

An object of the invention is to provide a compound which is capable to reduce the receptor activity of CXCR4.

Another object of the present invention is to provide a compound which is capable to influence proliferation of a cancer cell.

Another object of the present invention is to provide a compound which is capable to influence migration or homing of a cancer cell.

A still further object of the present invention is to provide a compound which is capable to influence the formation of metastases.

Another object of the present invention is to provide a compound which is capable to treat highly aggressive tumors so that the cancer is considerably inhibited or becomes a chronic disease.

Still another object of the present invention is to provide a compound which is capable to regulate and treat various diseases, such as immune and allergic diseases, tissue growth and nervous system regulation.

SUMMARY OF THE INVENTION

The objects of the invention are solved by any of the polypeptides of the invention. The polypeptides of the invention exhibit great therapeutic potential.

A polypeptide of the invention comprises the general amino acid sequence (written in the single letter code)

$$Z^1IX^2RWX^5X^6KX^8PX^{10}X^{11}SZ^3,$$

wherein
$X^2$=V, M or L, in particular L,
$X^5$=S or T,
$X^6$=K or R, in particular R,
$X^8$=V, M, L or F, in particular M,
$X^{10}$=Q or C, in particular C and
$X^{11}$=V, M or F, in particular V;

$Z^1$=0, $Z^2$, or <E, wherein $Z^2$=0 or is a modification of the N-terminal nitrogen atom of the peptide chain which modification forms together with the amino group of the N-terminal amino acid of the peptide a moiety having the structure —$NR^2R^3$ wherein $R^2$ and/or $R^3$ are independently from each other H or a substituted or unsubstitued acyl alkyl, aryl, aralkyl, cyclo alkyl and heterocyclo alkyl group;

$Z^3$=0, or $Z^4$, wherein $Z^4$=0 or is a modification of the C-terminal carboxyl group of the peptide chain, which modification forms together with the carboxyl group of the C-terminal amino acid of the peptide a moiety having the structure —C(O)—O—$R^1$ or —C(O)—$NR^2R^3$, wherein $R^1$ is a substituted or unsubstitued alkyl, aryl, aralkyl, cyclo alkyl and heterocyclo alkyl group; and wherein further abbreviations have the following meaning:

Cap=caproic acid (C$_6$ carboxylic acid), Aca=amino caproic acid, <E=pyro glutamate, Val=valeric acid (C$_5$ carboxylic acid), and Sul=sulfon amino acids.

In an embodiment of the invention the peptide of the invention comprises at least one of the following amino acid sequence:

```
                            (SEQ ID NO: 1)
IVRWSKKVPQVS (SEQ ID NO: 2)
IMRWSRKMPCVS (SEQ ID NO: 3)
ILRWSRKLPCVS (SEQ ID NO: 4)
ILRWSRKMPCVS (SEQ ID NO: 5)
ILRWTRKMPCVS (SEQ ID NO: 6)
ILRWSRKMPCMS (SEQ ID NO: 7)
ILRWSRKFPCVS (SEQ ID NO: 8)
ILRWSRKMPCFS (SEQ ID NO: 9)
ILRWSRKMPQFS,
and
                            (SEQ ID NO: 10)
IVRWSKKMPQVS.
```

According to the invention single or several amino acid residues in the sequence can been exchanged, deleted or added, or chemical modifications on single amino acids of said polypeptide can been introduced which result in an improved biological or pharmacological activity of the unmodified polypeptide of the invention. Respective methods for modifications are known to the skilled person.

Furthermore at least one side chain of an amino acid of said polypeptide can be chemically modified, in particular phosphorylated, amidated, acetylated, glycosylated, PEGylated, HESylated or combinations thereof.

The choice of the suitable functional group for the PEG derivative is based on the type of available reactive groups on the molecule that will be coupled to the PEG. For proteins, typical reactive amino acids include lysine, cysteine, histidine, arginine, aspartic acid, glutamic acid, serine, threonine, tyrosine. The N-terminal amino group and the C-terminal carboxylic acid can also be used as a specific site by conjugation with aldehyde functional polymers.

According to the invention the polypeptide according of the invention may comprise at least one D-amino acid. In particular the polypeptide of the invention may be composed by a chain of D-amino acids in a retro-inverso configuration of the chain of the polypeptide of the invention.

A further subject matter of the present invention is a medicament comprising at least one polypeptide of the invention and a pharmaceutically acceptable carrier. In one of the simplest embodiments to the polypeptide of the invention can be administered in water for infusion, physiological saline, or buffered aqueous solutions. Also other formulations are possible for example encapsulation in liposomes forming nanoparticles of various sizes, for example from 20 to 2.000 nm.

Typically, the peptide of the invention is administered in amounts of 10-1,000 mg/kg body weight for a time period sufficient to stop tumor growth. The time of administration is between two to ten weeks. The medicament of the invention is preferably suitable for oral, intravenous, intramuscular, intracutaneous, subcutaneous, intrathecal administration or present in form of an aerosol suitable for transpulmonary and intranasal administration, in particular encapsulated in liposomes; or for use in aqueous or liposomal packaging.

Subject matter of the present invention is also a polynucleotide coding for a polypeptide of the invention and/or its fragments, variants, derivatives and analogues. The polynucleotide of the invention may be constituted of DNA, RNA, genomic DNA or PNA. Also a polynucleotide hybridizing to a polynucleotide according to the invention that codes for a polypeptide of the invention is also subject of the present invention.

A further subject matter of the present invention is also a vector containing a polynucleotide according to the invention, as well as a genetically engineered host cell containing the vector according the invention.

A still further subject matter of the invention is an antibody directed against at least one polypeptide of the invention.

Yet another subject matter of the present invention is an antagonist/inhibitor compound directed against a polypeptide according to the invention.

Subject matter of the invention is also a peptide of the invention for use in the treatment of neurological diseases, in particular stroke, Parkinson's disease, Alzheimer's disease, multiple sclerosis; in the field of immunology in particular for the treatment of the WHIm-syndrom, lupus erythematosus and rheumatoid arthritis; in the field of oncology in particular for the treatment of cancers, in particular cancers showing the CRCX receptor such as cancer of the liver, pancreas, prostate, or breast cancer; for the treatment of lack of mobilization, proliferation and migration of stem cells, T-cell activation as well as support of immunoblasts such as CTL/PD-1; in the treatment of wounds caused by burning; for the treatment of antifibrosis; treatment or prevention of scars; for treatment of cardiologic disorders, in particular heart insufficiency; for the treatment of metabolic disorders, in particular diabetes; for the treatment of viral diseases, in particular infections with HIV-I, HIV-2, Cytomegalo virus, Herpes simplex virus (type 1 and 2), Varicella zoster virus, Hepatitis A and Hepatitis B virus, Influenza virus, Polio virus, Rhino virus, Rubella virus, Measles virus, Rabies virus, Rous sarcoma virus, Epstein-Barr Virus; and for the treatment of infections caused by bacteria and fungi, in particular Pseudomonas, Candida, S. aureus; for the treatment of infectious processes, abnormal infectious processes; treatment of growth disorders, treatment of neuronal diseases, disorders of the blood clotting cascade and hematopoiesis, vascular diseases, diseases of the immune system, and for improving wound and bone healing, pulmonary disorders, and allergies.

Another process for the manufacturing of a polypeptide according to the invention is solid-phase synthesis in terms of Merrifield synthesis or liquid-phase synthesis by methods known to the skilled person using protected amino acids, and its purification.

Still another process for the manufacturing of a polypeptide according to the invention can employ methods of heterologous expression known to the skilled person using common biotechnological vectors, and if necessary subsequent posttranslational or chemical modification.

Subject matter of the present invention is a diagnostic agent containing poly- or monoclonal antibodies according to the invention or containing the nucleic acid or mRNA coding for a polypeptide according to the invention.

A further subject matter of the invention is a diagnostic agent containing a polypeptide according to the invention or a polynucleotide according to the invention for test systems for assaying tissue, plasma, urine and cerebrospinal fluid levels of this substance, diagnostic agents and test systems detecting a polypeptide according to the invention for assaying tissue, plasma, urine and cerebro-spinal fluid levels of this substance by means of mass-spectrometric methods, such as MALDI-MS or ESI-MS, in connection with sample preparation by RP-HPLC, protein precipitation and/or solid-phase extraction. Preferably methods of mass spectrometry are used for the detection of minute quantities of the molecules in the range of femto or atto molar quantities.

Also, a diagnostic agent is subject of the invention which are containing a polypeptide according to the invention as markers for viral diseases, bacterial and fungal infections, inflammatory and neoplastic processes, and as markers in inflammatory processes, disturbed inflammation reactions, tumor diseases, growth disorders, diseases of the immune system, WHIm-syndrom, lupus erythematosus and as markers in bone diseases as well as others.

The invention is further described in more detail using the peptide IVRWSKKVPQVS (Seq. ID No. 1) and ILRWSRKMPQFS (Seq. ID No. 9) as a typical representative of the peptide of the invention.

EXAMPLES

Peptides

The peptides of Seq ID No. 1 and Seq ID No. 9 and various derivates thereof were synthesized by conventional solid-phase synthesis on a peptide synthesizer 9050 (Applied Biosystems) using Fmoc chemistry. The peptide was purified by RP chromatography, and its identity and purity were established by analytical RP-HPLC and MALDI-MS and LC-ESI-MS.

Cancer Cell Invasion Assay

The cancer cell invasion assay was performed on humanized rats (Eyol, E. et al., Oncology Reports, 28: 2177-2187, 2012). Pancreas carcinoma cells were implanted. The successful implant was observed by luminescent imaging as well as by an increase in CXCR4 expression.

After a successful implant of carcinoma cells, the rats were treated with a peptide according to Seq ID No. 1 and Seq. ID No. 9 respectively. The results after 1 week of therapy (1 w of therapy), after 2 weeks of therapy (2 w of therapy) and 2 weeks after end of therapy are depicted in the below tables.

Results for Peptide of Seq ID No. 1

| Amount of peptide | 1 w of therapy | 2 w of therapy | 2 w after end of therapy |
| --- | --- | --- | --- |
| 0 mg (control) | Tumor growth | Tumor growth | Tumor growth |
| 10 mg | No tumor growth | Tumor growth | Tumor growth |
| 20 mg | No tumor growth | Complete Remission | Complete Remission |
| 70 mg | No tumor growth | Remission | Complete Remission |
| 7 mg | Tumor growth (little) | No tumor growth | Tumor growth (little) |
| 70 mg | Tumor growth (little) | Tumor growth (little) | Tumor growth (little) |
| 70 mg | Partial Remission | | |
| 70 mg | Partial Remission | | |
| 35 mg | Partial Remission | | |
| 35 mg | Complete Remission | | |

Results for Peptide of Seq ID No. 9

| Amount of peptide | 1 w of therapy | 2 w of therapy | 2 w after end of therapy |
| --- | --- | --- | --- |
| 0 mg (control) | Tumor growth | Tumor growth | Tumor growth |
| 35 mg | Tumor growth (little) | Remission (little) | Tumor growth |
| 70 mg | Tumor growth | Partial Remission | Tumor growth |
| 35 mg | Complete Remission | | |
| 35 mg | Complete Remission | | |
| 70 mg | Partial Remission | | |
| 70 mg | Partial Remission | | |

Rats without therapy died after tumor implant within few days.

Rats with therapy using the peptides of the present invention survived over at least two weeks. The tumor growth was stopped and depending on the concentration a partial or even complete remission of the tumor was observed. No toxic effect of the peptides was observed.

SEQUENCE LISTING
<110> Neopep Pharma GmbH & Co. KG

<120> Polypeptides for the Treatment of Diseases

<130> 182081WO

<150> EP17190152.3

<151> 2017-09-08

<150> EP17205238.3

<151> 2017-12-04

SEQ ID No. 1
Ile Val Arg Trp Ser Lys Lys Val Pro Gln Val Ser

SEQ ID No. 2
Ile Met Arg Trp Ser Arg Lys Met Pro Cys Val Ser

SEQ ID No. 3
Ile Leu Arg Trp Ser Arg Lys Leu Pro Cys Val Ser

SEQ ID No. 4
Ile Leu Arg Trp Ser Arg Lys Met Pro Cys Val Ser

SEQ ID No. 5
Ile Leu Arg Trp Thr Arg Lys Met Pro Cys Val Ser

SEQ ID No. 6
Ile Leu Arg Trp Ser Arg Lys Met Pro Cys Met Ser

SEQ ID No. 7
Ile Leu Arg Trp Ser Arg Lys Phe Pro Cys Val Ser

SEQ ID No. 8
Ile Leu Arg Trp Ser Arg Lys Met Pro Cys Phe Ser

SEQ ID No. 9
Ile Leu Arg Trp Ser Arg Lys Met Pro Gln Phe Ser

SEQ ID No. 10
Ile Val Arg Trp Ser Lys Lys Met Pro Gln Val Ser

---

SEQUENCE LISTING

<160> NUMBER OF SEQ ID NOS: 10

<210> SEQ ID NO 1
<211> LENGTH: 12
<212> TYPE: PRT
<213> ORGANISM: human

<400> SEQUENCE: 1

Ile Val Arg Trp Ser Lys Lys Val Pro Gln Val Ser
1               5                   10

<210> SEQ ID NO 2
<211> LENGTH: 12
<212> TYPE: PRT
<213> ORGANISM: human

<400> SEQUENCE: 2

Ile Met Arg Trp Ser Arg Lys Met Pro Cys Val Ser
1               5                   10

<210> SEQ ID NO 3
<211> LENGTH: 12
<212> TYPE: PRT
<213> ORGANISM: human

<400> SEQUENCE: 3

Ile Leu Arg Trp Ser Arg Lys Leu Pro Cys Val Ser
1               5                   10

<210> SEQ ID NO 4
<211> LENGTH: 12
<212> TYPE: PRT
<213> ORGANISM: human

<400> SEQUENCE: 4

Ile Leu Arg Trp Ser Arg Lys Met Pro Cys Val Ser
1               5                   10

<210> SEQ ID NO 5
<211> LENGTH: 12
<212> TYPE: PRT
<213> ORGANISM: human

<400> SEQUENCE: 5

Ile Leu Arg Trp Thr Arg Lys Met Pro Cys Val Ser
1               5                   10

<210> SEQ ID NO 6
<211> LENGTH: 12

```
<212> TYPE: PRT
<213> ORGANISM: human

<400> SEQUENCE: 6

Ile Leu Arg Trp Ser Arg Lys Met Pro Cys Met Ser
1               5                   10

<210> SEQ ID NO 7
<211> LENGTH: 12
<212> TYPE: PRT
<213> ORGANISM: human

<400> SEQUENCE: 7

Ile Leu Arg Trp Ser Arg Lys Phe Pro Cys Val Ser
1               5                   10

<210> SEQ ID NO 8
<211> LENGTH: 12
<212> TYPE: PRT
<213> ORGANISM: human

<400> SEQUENCE: 8

Ile Leu Arg Trp Ser Arg Lys Met Pro Cys Phe Ser
1               5                   10

<210> SEQ ID NO 9
<211> LENGTH: 12
<212> TYPE: PRT
<213> ORGANISM: human

<400> SEQUENCE: 9

Ile Leu Arg Trp Ser Arg Lys Met Pro Gln Phe Ser
1               5                   10

<210> SEQ ID NO 10
<211> LENGTH: 12
<212> TYPE: PRT
<213> ORGANISM: human

<400> SEQUENCE: 10

Ile Val Arg Trp Ser Lys Lys Met Pro Gln Val Ser
1               5                   10
```

The invention claimed is:

1. A polypeptide having the general amino acid sequence written in the single letter code $Z^1IX^2RWX^5X^6KX^8PQX^{11}SZ^3$, wherein
$X^2$=V, M or L,
$X^5$=S,
$X^6$=K or R,
$X^8$=V, M, L or F,
$X^{11}$=V, M or F,
$Z^1$=0, $Z^2$, or pyro glutamate, wherein $Z^2$ is a modification of the N-terminal nitrogen atom of the peptide chain which modification forms together with the amino group of the N-terminal amino acid of the peptide a moiety having the structure —$NR^2R^3$ wherein $R^2$ and/or $R^3$ are independently from each other H or a substituted or unsubstituted acyl, alkyl, aryl, aralkyl, cyclo alkyl or heterocyclo to alkyl group;
$Z^3$=0, or $Z^4$, wherein $Z^4$ is a modification of the C-terminal carboxyl group of the peptide chain, which modification forms together with the carboxyl group of the C-terminal amino acid of the peptide a moiety having the structure —C(O)—O—$R^1$ or —C(O)—$NR^2R^3$, wherein $R^1$ is a substituted or unsubstituted alkyl, aryl, aralkyl, cyclo alkyl or heterocyclo alkyl group; and $R^2$ and $R^3$ are defined as above.

2. The polypeptide according to claim 1, selected from the group consisting of polypeptides having the amino acid sequence IVRWSKKVPQVS (SEQ ID No. 1), ILRWSRKMPQFS (SEQ ID NO: 9), and IVRWSKKMPQVS (SEQ ID NO: 10).

3. The polypeptide according to claim 1, wherein at least one side chain of an amino acid of said polypeptide is phosphorylated, amidated, acetylated, glycosylated, PEGylated, HESylated or combinations thereof.

4. The polypeptide according to claim 1, wherein the polypeptide comprises at least one D-amino acid.

5. A medicament comprising at least one polypeptide according to claim 1 and a pharmaceutically acceptable carrier.

6. The medicament according to claim 5 suitable for oral, intravenous, intramuscular, intracutaneous, subcutaneous, intrathecal administration or in form of an aerosol suitable for transpulmonary administration, encapsulated in liposomes; or for use in aqueous or liposomal packaging.

* * * * *